United States Patent [19]

Geiler et al.

[11] Patent Number: 5,206,710
[45] Date of Patent: Apr. 27, 1993

[54] METHOD AND APPARATUS FOR THERMOWAVE ANALYSIS

[75] Inventors: Hans-Dieter Geiler; Matthias Wagner; Peter Kowalski, all of Jena, German Democratic Rep.

[73] Assignee: Jenoptik Jena GmbH, Jena, Fed. Rep. of Germany

[21] Appl. No.: 765,646

[22] Filed: Sep. 25, 1991

[30] Foreign Application Priority Data

Nov. 2, 1990 [DE] Fed. Rep. of Germany ....... 4035266

[51] Int. Cl.$^5$ ........................................... G01N 21/17
[52] U.S. Cl. ..................... 356/432; 356/447
[58] Field of Search .................. 356/432, 432 T, 445, 356/447; 250/351, 339, 338.5; 374/5, 57

[56] References Cited

U.S. PATENT DOCUMENTS

| 4,044,257 | 8/1977 | Kreuzer ............................ 356/432 |
| 4,579,463 | 4/1986 | Rosencwaig et al. .............. 356/432 |
| 4,634,290 | 1/1987 | Rosencwaig et al. .............. 356/432 |
| 4,636,088 | 1/1987 | Rosencwaig et al. .............. 356/432 |

Primary Examiner—Richard A. Rosenberger
Attorney, Agent, or Firm—Jordan and Hamburg

[57] ABSTRACT

A method and apparatus for thermowave analysis employs a single laser beam, which has an additive, two-frequency, intensity modulation, and is directed onto the object. The amplitude of the mixed frequency of the discrete modulation frequencies, which is not contained in the exciting beam, is analyzed as response signal. By obtaining a reference signal from the exciting beam and forming the difference between this exciting beam and the measurement signal, noise suppression and a lowering of the limit of sensitivity are achieved in an advantageous manner.

32 Claims, 4 Drawing Sheets

METHOD AND APPARATUS FOR THERMOWAVE ANALYSIS

BACKGROUND OF THE INVENTION

The invention relates to a method and apparatus for thermowave analysis using the single-beam method. It may be employed in the measurement of geometric, thermal, electronic and elastomechanical material parameters of surface layers by evaluating photothermal response signals from the surface layers. The contactless, non-destructive, method is primarily useful in coating technology as a test method for quality control.

Photothermal spectroscopic methods are known for the contactless and non-destructive determination of parameters of layers. The physical principles and the basic solutions are compiled and described, for example, in "Photoacoustic and Thermal Wave Phenomena in Semiconductors", edited by A. Mandelis for North-Holland, N.Y. 1987.

In a known method, which was developed by A. Rosencwaig, a periodic intensity modulated pumping laser stimulates a thermowave in a layer, which in turn locally modulates the refractive index, so that the modulated optical reflections (MOR) can be measured with a second, so-called test laser beam (U.S. Pat. No. 4,579,463). The signals are processed, preferably by means of the lock-in technique, in order to determine the phase and amplitude of the MOR. This method requires the use of 2 lasers of different wave lengths and, to ensure a reflection signal which can be evaluated quantitatively, the concentric arrangement of pumping beam and test beam with a vertical incidence on the layer. Moreover, the radius of the test beam should be at most half the radius of the pumping beam.

The solutions proposed in U.S. Pat. Nos. 4,634,290 and 4,636,088 and European patents 0 162 681 and 0 291 276 require, aside from a high optical precision for the defined focus location additional optical expense (telescope) for matching the waists of laser beams and an adjusting expense for placing the waists on the surface of the layer. In addition, the background noise of the test laser represents a limiting factor for the resolution capacity, so that, with the usual requirements of $\delta R/R < 10^{-6}$, lasers must be used, which are highly stabilized with respect to noise. Such lasers further increase the costs. When the double-beam method is used as an in situ measurement method with a large distance from the objective to the object, for example, in coating chambers, the optical adjustment and the stability are barely manageable. Single-beam methods are also known for measuring the MOR (L. Chen et al. in: Appl. Phys. Lett. 50 (1987) 1349; A. Loerincz, L. Andor in: Photoacoustic and Photothermal Phenomena, P. Hes, J. Pelzl (editors) Springer Verlag, Heidelberg, 1968, page 486.). In these single-beam methods, the reflected pumping laser radiation is detected. To separate the MOR from the reflected, modulate pumping intensity, use is made of the fact that, during the modulation by the thermowave, upper harmonic waves of the modulation frequency are formed. This enables a lock-in detection of the second upper harmonic wave. The disadvantage of this method is that the modulator of the pumping laser also produces upper harmonic waves, which distort the measurement signal. The method of the precise square wave modulation of the pumping laser proposed by A. Loerincz (Appl. Phys. B47 (1988) 40), is associated with an extremely high expenditure for the modulation at higher modulation frequencies in the MHz range (build-up times in the ps range). In this reference, the thought is also expressed of separating from the first refraction order of the reflected laser beam, which is produced by the thermowave, the MOR information contained therein by a phase-contrast method from the modulated pumping intensity. Because of the finite width of the diffraction zone, the reduction of the MOR pump upper harmonic wave ratio to $10^{-7}$ is hardly possible. The same is true for the compensation.

SUMMARY OF THE INVENTION

The invention is directed to the reduction of the technical effort of optical thermowave analysis and the lowering of the sensitivity limit in such analysis.

The concept of the invention is based upon the fact that the excitation of the object and the detection of the transmission or reflection modulated by the object are to be accomplished with a single optical beam, which is directed onto the object and the intensity of which is modulated with two frequencies. This modulation can be produced by a light source, which can be modulated and on which the two modulation frequencies are impressed, by dividing one beam into two partial beams, modilating them separately and subsequently bringing them together to form one beam or by using two, separate, individually modulated light sources and combining the partial beams so created. However, in the event of the production of the beam from two partial beams which have been split from one light source, the possibility of interference of the partial beams with one another must be excluded, in order to suppress the undesirable generation of mixed products of both frequencies.

The thermowave reaction, which is initiated by the additive, two-frequency modulation of the invention that acts effectively for the object as excitation with the arithmetic mean of the two frequencies, is found in the portion of the beam leaving the object in the form of mixed products of the two frequencies, which are not contained in the excitation beam because of the additivity of the modulation and therefore can be detected by means of a frequency-selective device.

Advisably, the difference between the two frequencies modulating the beam is used for detecting the transmission or reflection modulated by the object, since this difference can easily be placed in low frequency regions. This produces an advantageous effect on the costs of the electronic measurement. For the evaluation of the cumulative frequency of the two modulation frequencies, which is also possible, the intensity amplitude must be evaluated and the phase shift must be analyzed.

In addition, it is advantageous to undertake the detection of the modulated transmission or reflection by forming the difference between the measurement signals of the intensity of the beam portion leaving the object once again and of the intensity of a partial beam decoupled from the incident beam.

The intensities used to form the difference are equalized during the measuring process advisably by an element of controllable transmission, so that the temporal average of the difference of the measurement signals is zero. This principle of measuring has the advantage that the particular portion of the intensity noise of the light source is suppressed, which exceeds the shot noise of the photon beam of the detectors and of which, in the event that only the intensity of the beam portion affected by the object is measured, particularly those contributions, which originate from the regions of the detected mixed frequency as well of the modulation frequencies that are displaced by the mixed frequency, have an interfering effect. As a result, the absolute sensitivity is no longer determined by the specific noise properties of the light source, but only by the intensity of the light source and the noise properties of the detection system. Comparatively very noisy light sources, such as lasers of lesser stability, can also be used for the measurement method.

The range of applications of the inventive method can also be extended to those thermowave reactions of the object which essentially do not bring about a modulation of the transmission or reflection capability and instead lead to position and form modulations of the beam. This occurs by inserting diaphragms to trim the beam, depending on their position and/or shape, at a suitable place in the path of the beam affected by the object. In addition, diaphragms can be used in this beam path in a conjugated object plane for the purpose of limiting the measurement field.

The conversion of the method of the invention into apparatuses, which fully bring to bear the promised advantageous effects, can be differentiated essentially by the method in which the additive two-frequency modulation is realized technically. Moreover, the generation of a single light beam, which is directed on the object, is divided quite generally on the basis of whether the light of one source or of two mutually independent sources is used. The first case can then be differentiated further on the basis of whether the two-frequency modulation is realized within the light source or whether a beam division and separate modulation of the partial beams is realized.

The apparatus of one embodiment of the invention can be realized advantageously by using a laser diode as a light source, to which both modulation frequencies are supplied. Depending on whether the object is to be analyzed in transmission or reflection, either an optical system, equivalent to the objective, and the measurement detector are connected in series with the object, or a beam-decoupling element for the reflected beam portion is disposed in the beam path after the twice used objective. It has proven to be advantageous for the suppression of the laser noise that a differential amplifier, which is connected at its inverting input to a reference detector, the input signal of which is decoupled from the unaffected beam of the laser source by means of a semitransparent mirror, is disposed in the electronic evaluating system ahead of the frequency-selective device. Furthermore, the laser source advisably is comprised of an unmodulated laser and a modulating optical element, to which the two modulation frequencies are supplied. For this purpose, the modulating, optical element advantageously is an acoustooptical modulator.

The apparatus can be configured advantageously with both partial beams initially polarized linearly in the same direction and a glass plate, positioned in each of the partial beam paths below the Brewster angle, disposed so that the portion of the beam, reflected by the glass plates, is in each case reflected along a common axis. In this arrangement a $\lambda/2$ plate disposed on this axis between the glass plates and a reference detector is disposed on this axis in the direction of the reflected beam portions outside of the interval between the glass plates and a $\lambda/2$ plate present in one of the partial beam paths between the glass plate and the beam-splitting prism.

This construction can be expanded advantageously in two modifications. On the one hand, the measurement detector is disposed on the common axis of the glass plates opposite to the reference detector and the beam-splitting prism is designed in the form of a polarization separator. On the other, complete decoupling of the beam incident on the object and the beam reflected by the object can be achieved by orienting the incident laser beam parallel to the axis of the objective, so that the reflected beam also is centrosymmetrical with respect to the objective axis and also parallel to this axis and that the measurement detector is in the beam path of the reflected beam. In both modifications, it is advantageous to dispose, immediately in front of the reference detector, an element with controllable transmission for equalizing the temporal average value of the measurement detector signal and the reference detector signal to zero.

A further apparatus of the invention is complemented advantageously owing to the fact that a semitransparent mirror is disposed between the beam-splitting prism and the objective, which (analogously to the first described apparatus) decouples a portion of the incident laser beam onto a reference detector, the measurement detector signal and the reference detector signal being supplied to the inputs of a differential amplifier connected in series with the frequency selective device. Moreover, it is advantageous, if the beams of the two laser sources are polarized perpendicularly to one another, for the beam-splitting prism to simultaneously comprise a polarization separator and to provide a polarization filter with the same orientation ahead of the measurement detector and ahead of the reference detector, in order to screen those parts of the laser beam for recording, which permit the phase shift between the exciting modulation signal and the response signal to be determined.

With the method and the different apparatuses of the invention, it is possible to reduce appreciably the technical effort involved in thermowave analysis and, with the help of slight supplements (e.g. a reference branch) to lower the sensitivity limit significantly.

BRIEF FIGURE DESCRIPTION

The invention is described below in greater detail with respect to the drawings, wherein.

DISCLOSURE OF PREFERRED EMBODIMENTS

Figure 1:
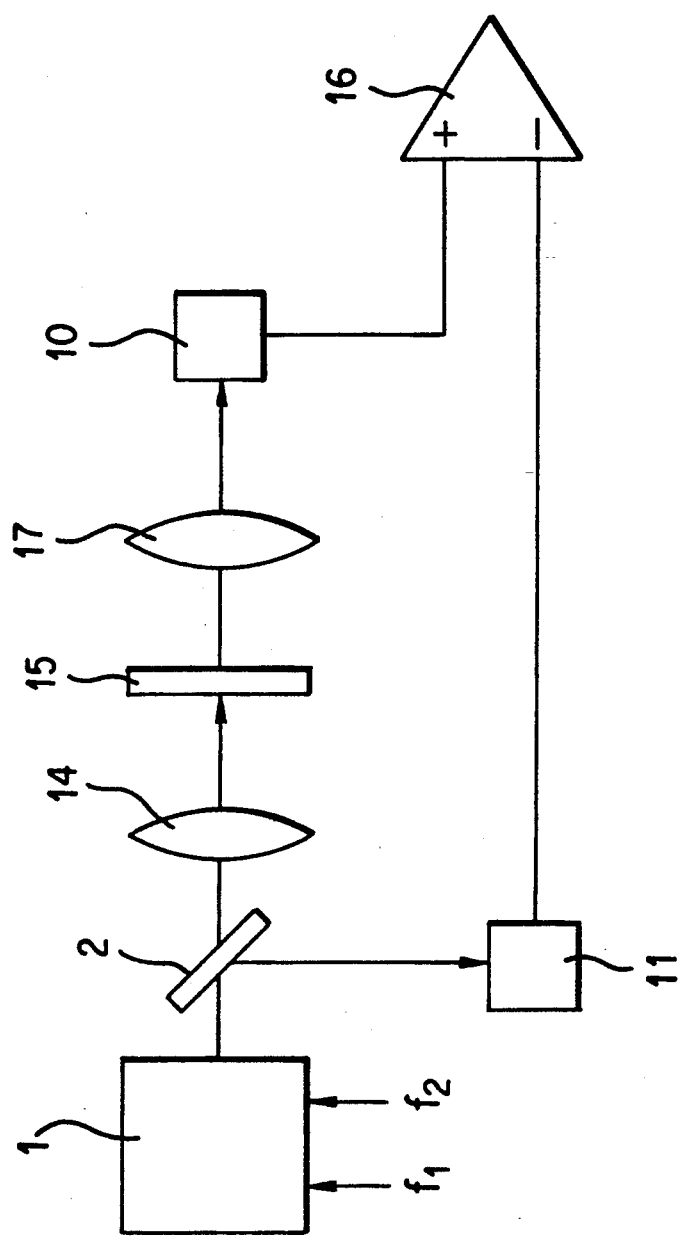
FIG. 1 shows the basic, inventive construction of an apparatus for thermowave analysis in the transmission mode.

FIG. 1 illustrates a basic embodiment of the inventive method. A single optical beam is focussed by an objective 14 on the object 15 that is to be analyzed. Particularly for reasons of the power required, the optical beam should be a laser beam. Pursuant to the invention, the laser beam has an intensity modulation spectrum with two discrete frequencies $f_1$ and $f_2$. As a source for this purpose, a laser diode $1'$ is desirably used, to which excitation at both frequencies $f_1$ and $f_2$ are supplied. As a result, the object 15 experiences an effective excitation with the arithmetic mean of the frequencies $f_1$ and $f_2$ and shows a thermowave reaction which contains mixed products of the frequencies $f_1$ and $f_2$ in the portion of the beam leaving the object. Because of the additivity of the excitation, these mixed products are not contained in the incident beam. According to FIG. 1, the thermowave reaction of the object 16 is transmitted via an optical system 17 which is equivalent to the objective 14, to a measurement detector 10. On the assumption that laser source 1 produces extremely little noise, the signal of the measurement detector 10 is sufficient for generating the amplitude of the mixed frequency by a frequency-selective device for the evaluation, without absolutely requiring the elements of the semitransparent mirror 2, the reference detector 11 and the differential amplifier 16. With this reference branch, which is shown in FIG. 1 and which decouples a portion of the laser beam that is directed to the object 15, it is, however, possible to suppress the laser noise effectively, if the incoming measurement and reference signals are equalized to the average temporal difference value of zero. The differential amplifier signal which reaches the frequency-selective device 30 for evaluation, can moreover, also be used for the equalization of the intensities of the measurement signal and the reference signal. This equalization is not shown in FIG. 1.

Figure 2:
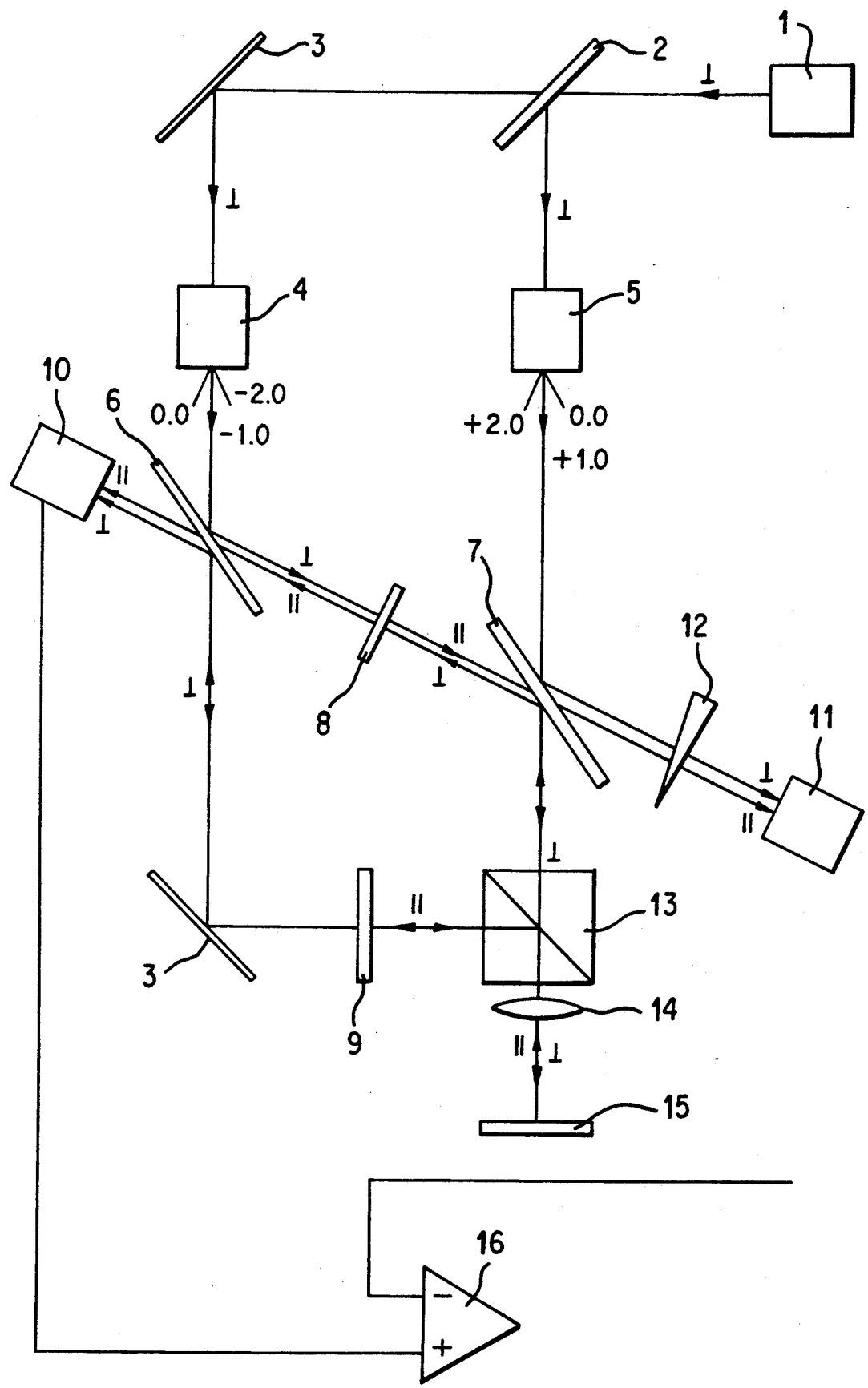
FIG. 2 shows the inventive apparatus with a split laser beam in the reflection mode with a special detector balance device.

FIG. 2 illustrates the beam control for the reflection mode. A cw laser is used for the laser source 1 and two acoustooptical modulators 4 and 5 are used for intensity modulation of two partial beams obtained by beam splitting. The laser beam, polarized perpendicularly to the plane of the drawing, is split by the use of a semitransparent mirror 2 and a tilted mirror 3 into two portions of equal intensity. The partial beams, so formed, pass through the modulators 4 and 5, respectively. After their modulation, the partial beams strike glass plates 6, 7, respectively. The glass plates 6 and 7 are in each case oriented below the Brewster angle and disposed so that the portions of the beam reflected at the glass plates 6 and 7, are reflected along a common axis, on which a $\lambda/2$ plate 8 is disposed between the glass plates 6 and 7, so that the portion of the beam reflected at the glass plate 6, after a polarization rotation through 90°, passes through glass plate 7 and, together with the portion of the beam reflected from glass plate 7, strikes the reference detector 11. The detector 11 is also on the common axis. The portion of the beam traversing the glass plate 6 is deflected by a further mirror 3, passes through a $\lambda/2$ plate 8 and, together with the beam portion of the second beam, which has traversed the glass plate 7, is focused via a polarization separating beam-splitting prism 13 on the object 15 as a beam by means of the objective 14. The beam which is reflected by the object 15 is split once again in the beam-splitting prism 13 in accordance with the two polarization directions thereof. The beam portions so produced traverse the paths previously traversed in opposite directions via the two partial beams up to the glass plates 6 and 7 respectively. The portion reflected at glass plate 6, passes through the $\lambda/2$ plate 8 and the glass plate 6 and, together with the portion reflected at the glass plate 6, is passed along the above-mentioned common axis of the glass plates 6 and 7 to the measurement detector 10. Measurement and reference signals once again are subtracted from one another in a differential amplifier 16. The control signal for the already indicated intensity equalization between the measurement detector 10 and the reference detector 11 is also obtained by the differential amplifier 16. With said control signal, the element 12 with controllable transmission optically adjusts the intensity to the temporal average value of zero. In the embodiment of FIG. 2, however, it is not possible to exclude the reaction of the beam portions which are reflected at the object 15 on the laser source 1.

Figure 3:
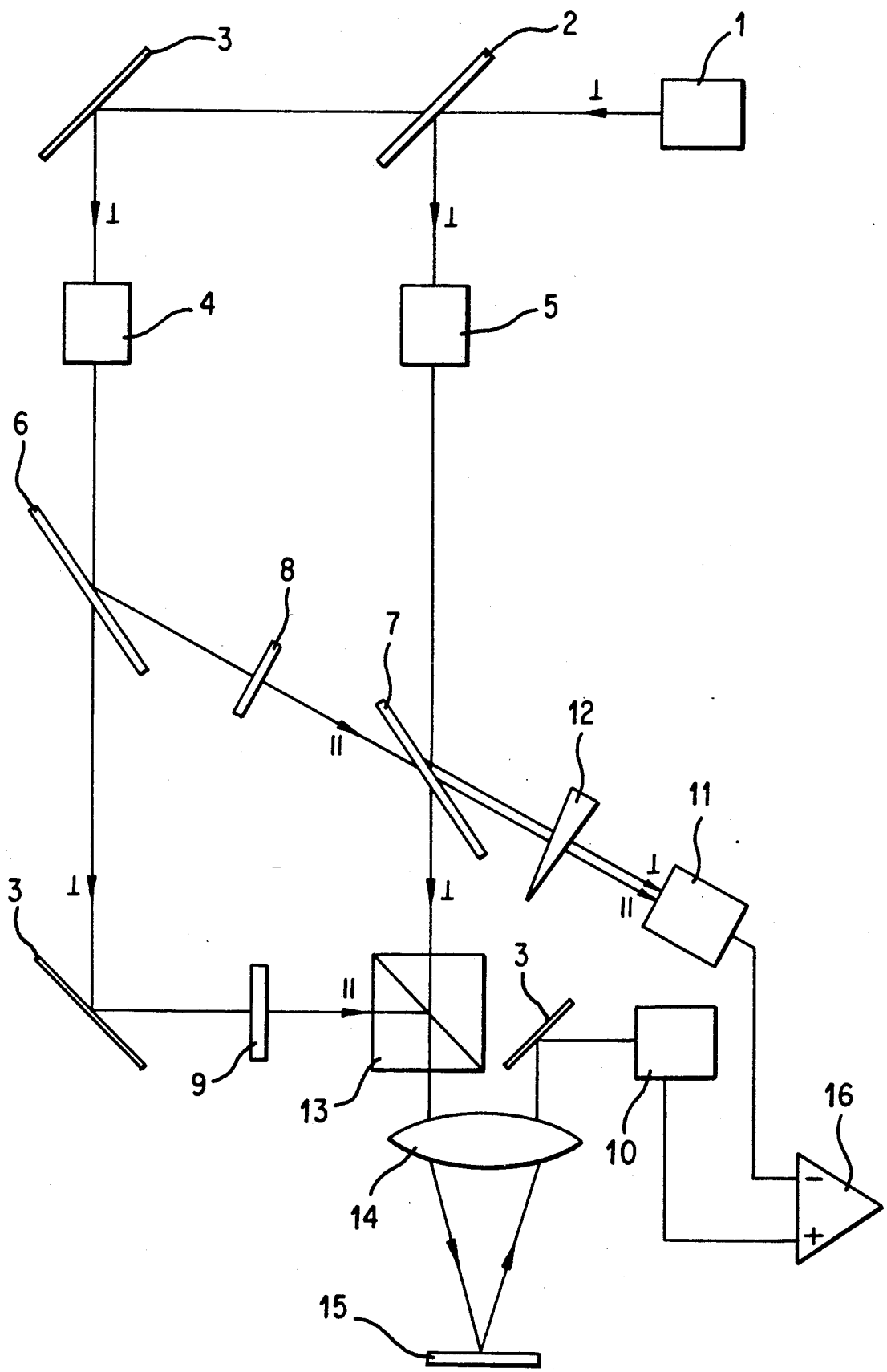
FIG. 3 shows a special embodiment of the apparatus with a split laser beam for the complete decoupling of the reflected beam portions.

In the invention of FIG. 3 the two partial beams are produced in an identical manner and are combined in the beam-splitting prism 13. This objective 14, with its objective axis, is displaced from the excitation beam direction, so that the excitation beam and the reaction beam of the object 15 are centrosymmetrical with respect to the objective axis and the reaction beam, which is reflected at the object 15, enters the measurement detector 10 via a mirror 3. All the remaining elements and their functions are retained, as described with reference to FIG. 2.

It must still be pointed out that in the embodiments of FIGS. 2 and 3, wherein two partial beams are produced by splitting the light of a laser source 1, the interference ability of the partial beams must be suppressed, so as not to produce, by interferences, mixed products of the modulation frequencies $f_1$ and $f_2$ which would distort the measurement results. For this purpose, there are essentially four possibilities, which optionally are used in the partial beam paths. Two of the possibilities are indicated in FIG. 2. These are, on the one hand, the generation of a sufficiently large wave length difference in the partial beam paths and, on the other, the utilization of different diffraction orders for the acoustooptical modulators 4 and 5. For the latter modification the refraction orders used in the two partial beams must differ by at least the value of one. Furthermore, the ability of the partial beams to interfere can be eliminated by the use of different carrier frequencies of the acoustooptical modulators 4 and 5, so that the wave lengths of the partial beams can be altered slightly. The fourth and last possibility is contained in FIGS. 2 and 3 and relates to the polarization direction of the partial beams perpendicular to one another, the polarization directions, which are perpendicular to one another, fulfilling a double function here for decoupling the reference value and the measurement value.

Figure 4:
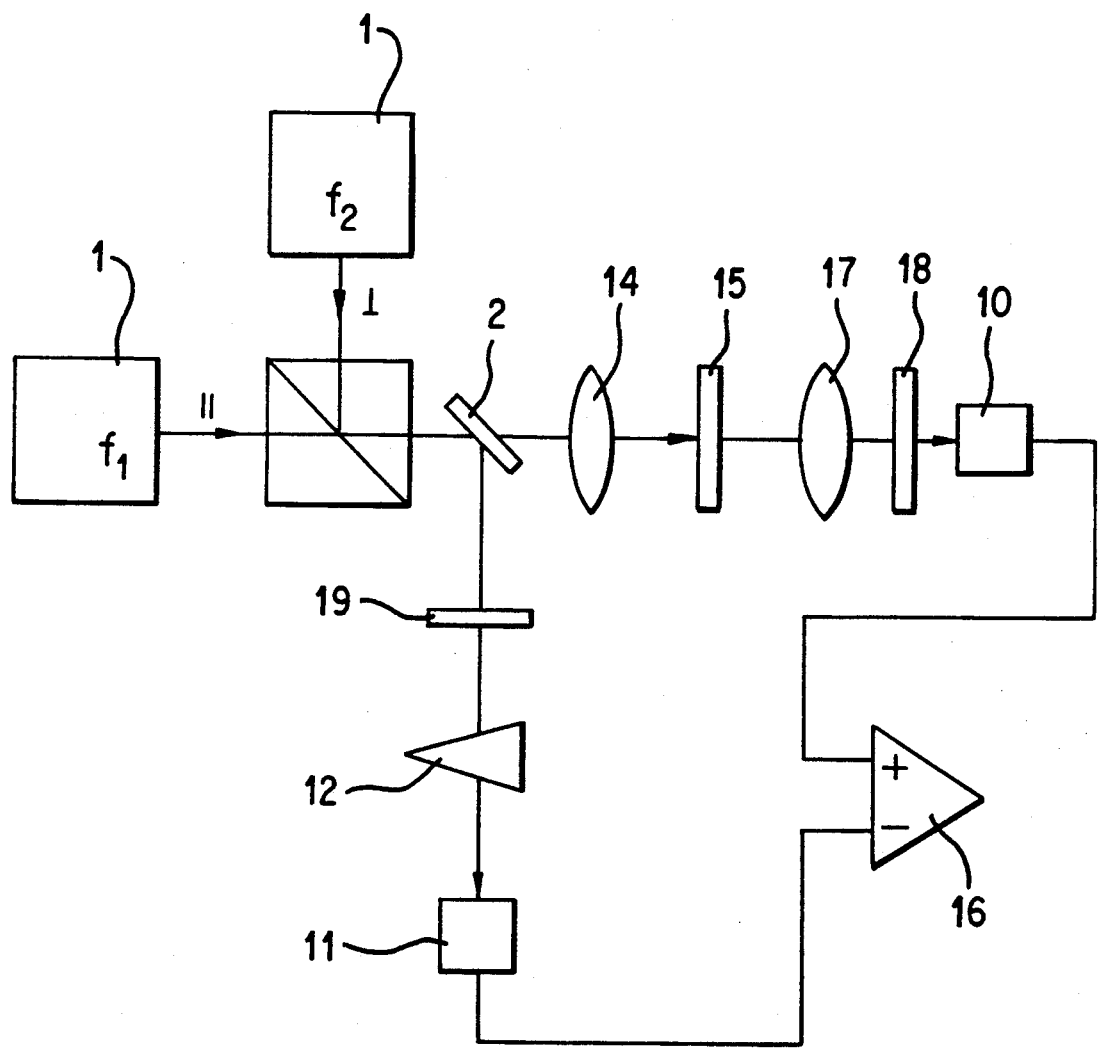
FIG. 4 shows a transmission apparatus with two separate laser sources and polarization decoupling of the measurement and reference branches.
Figure 1:
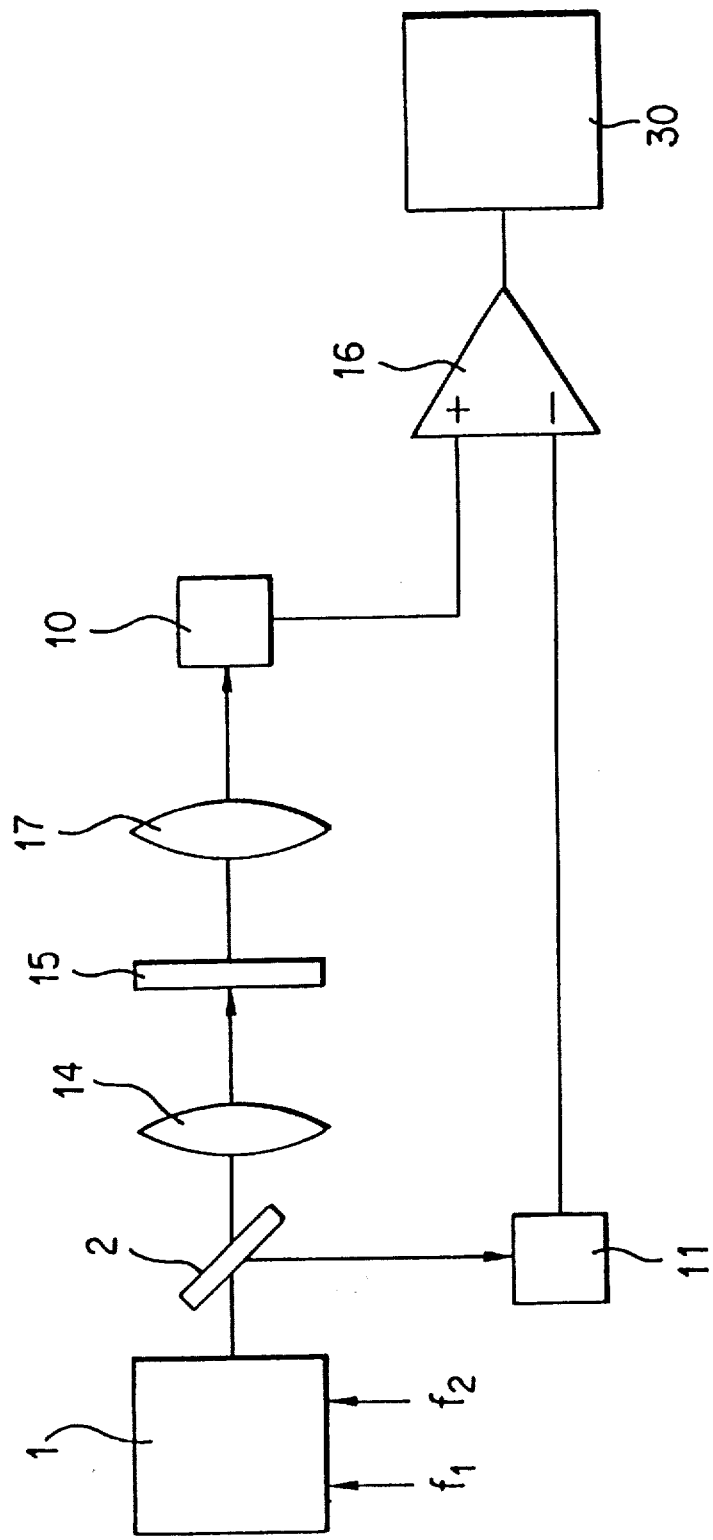
Figure 2:
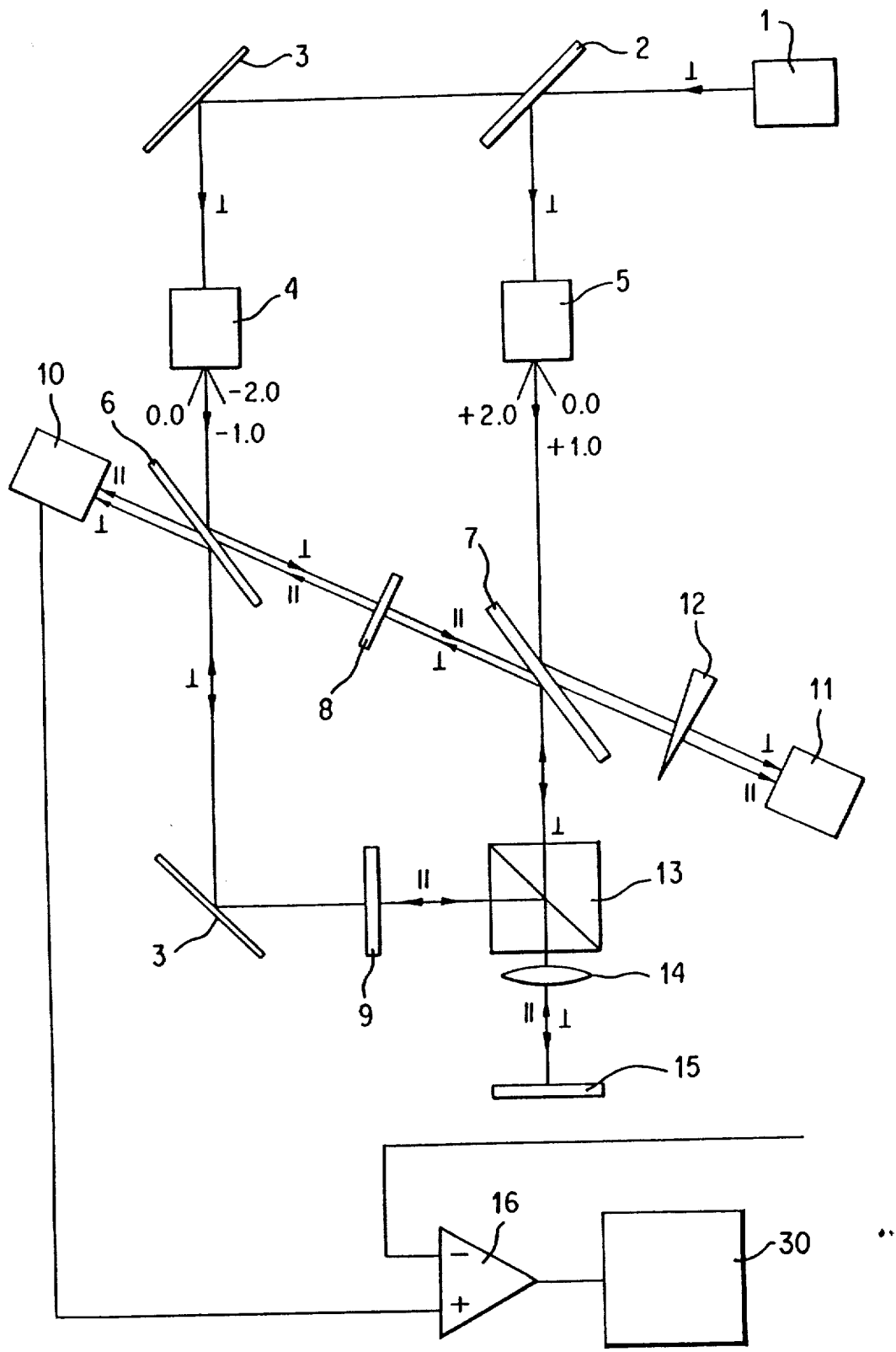
Figure 3:
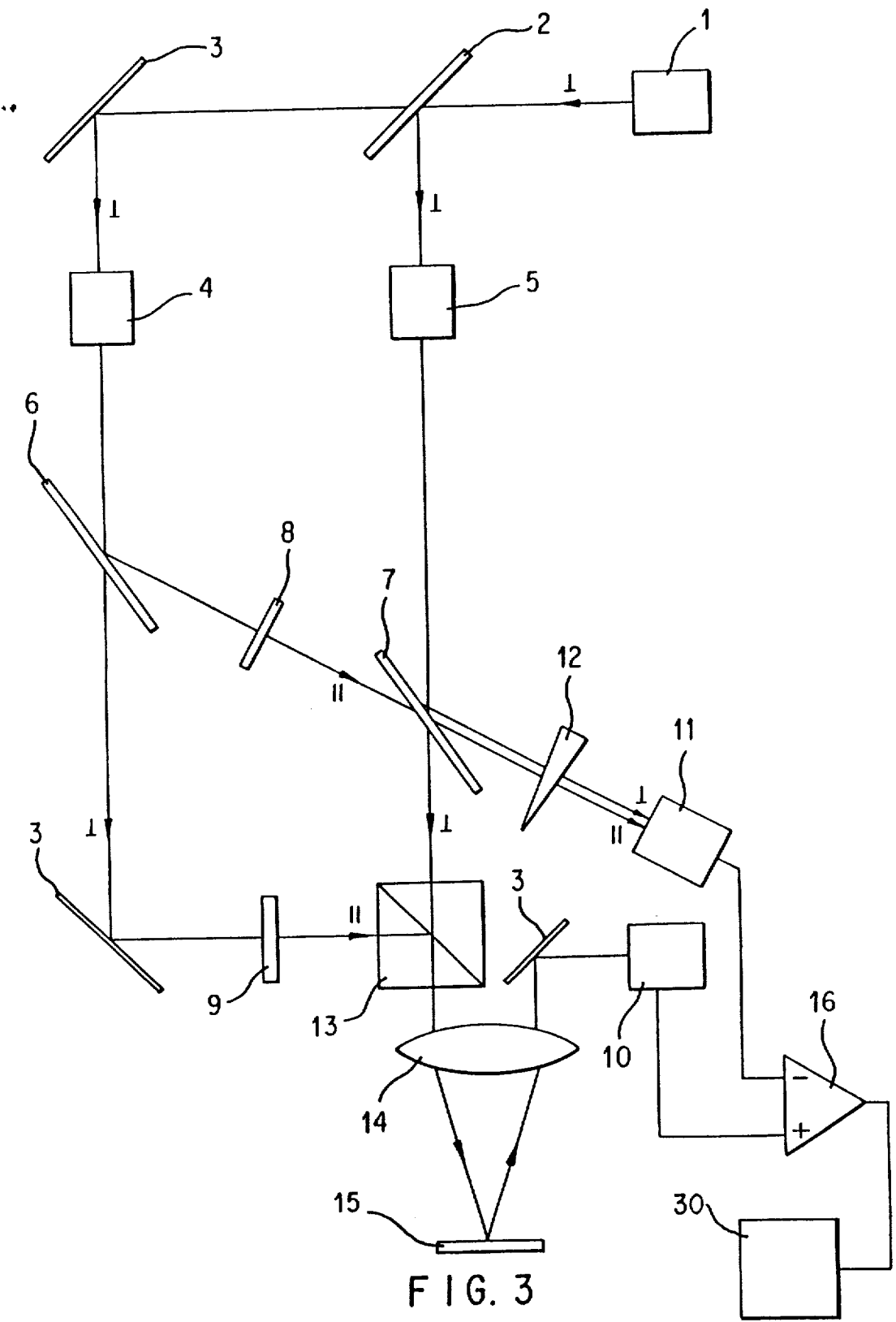
Figure 4:
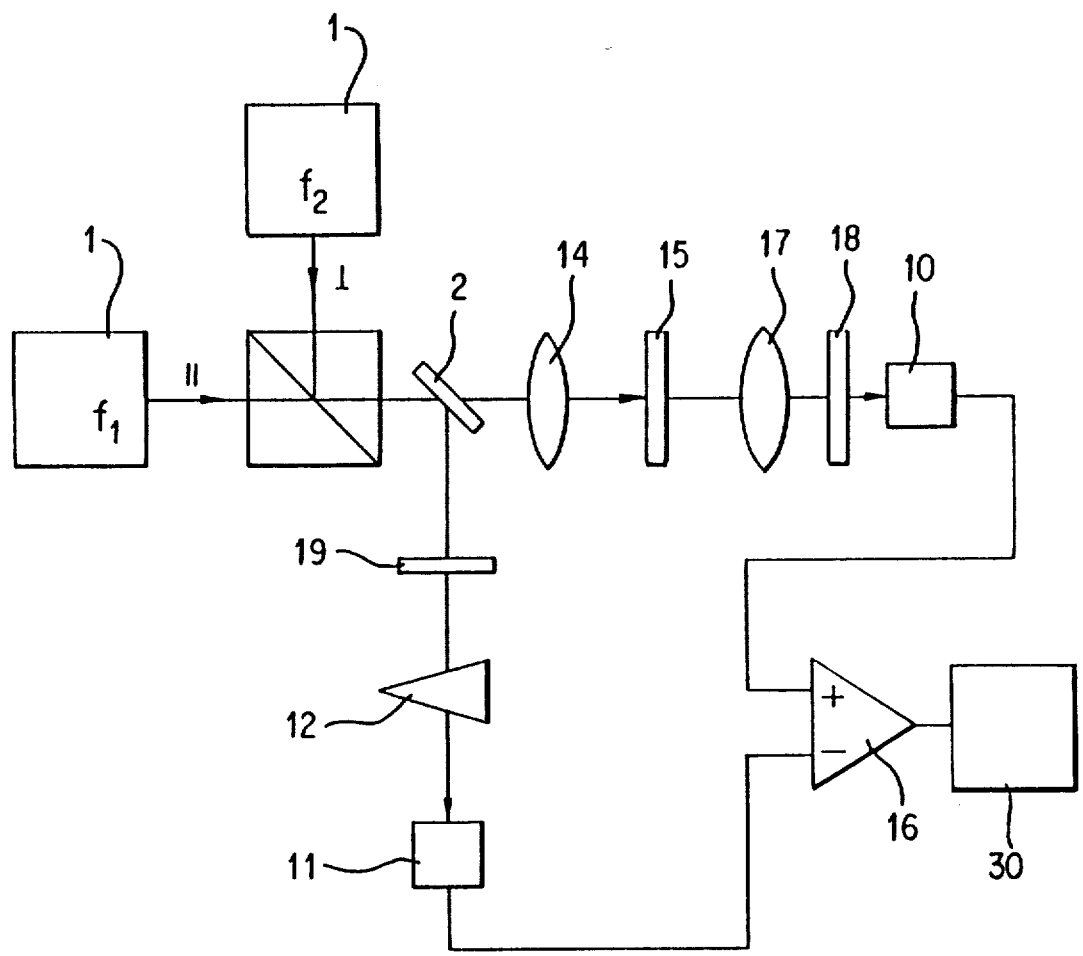
Figure 1:
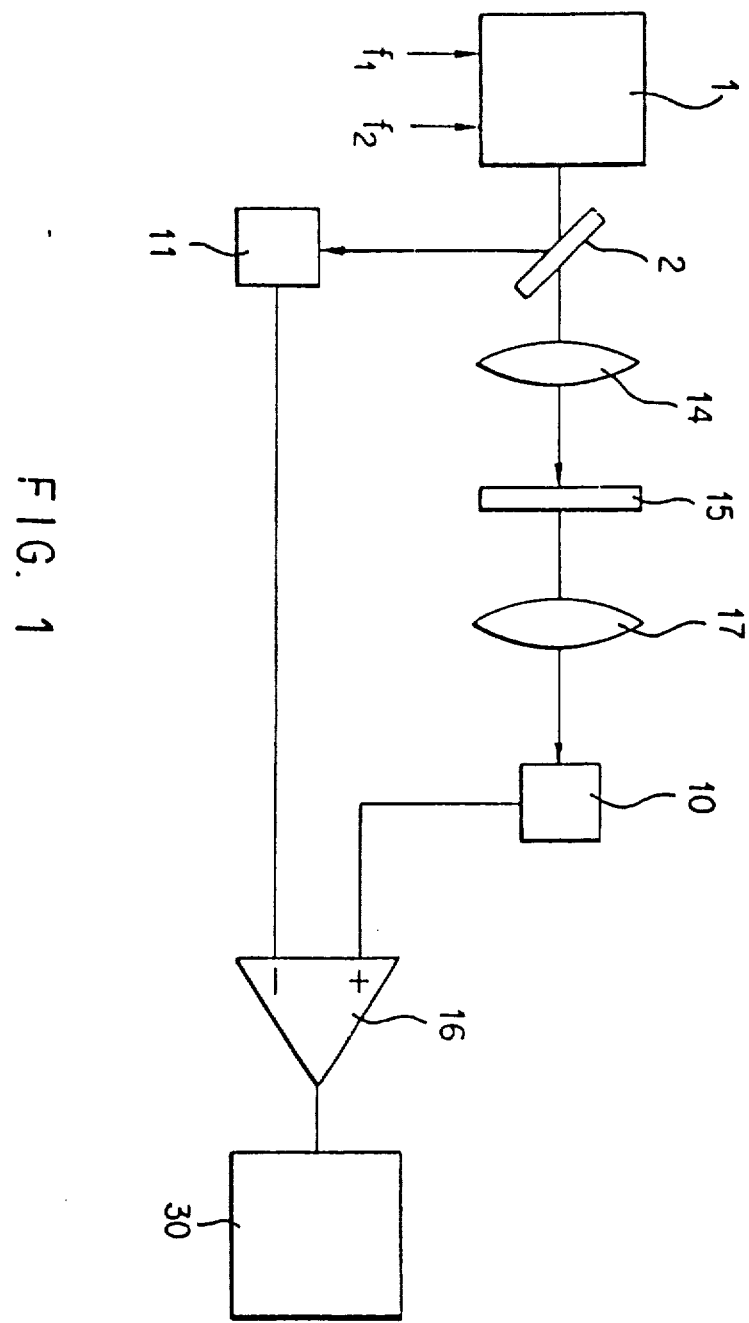
Figure 2:
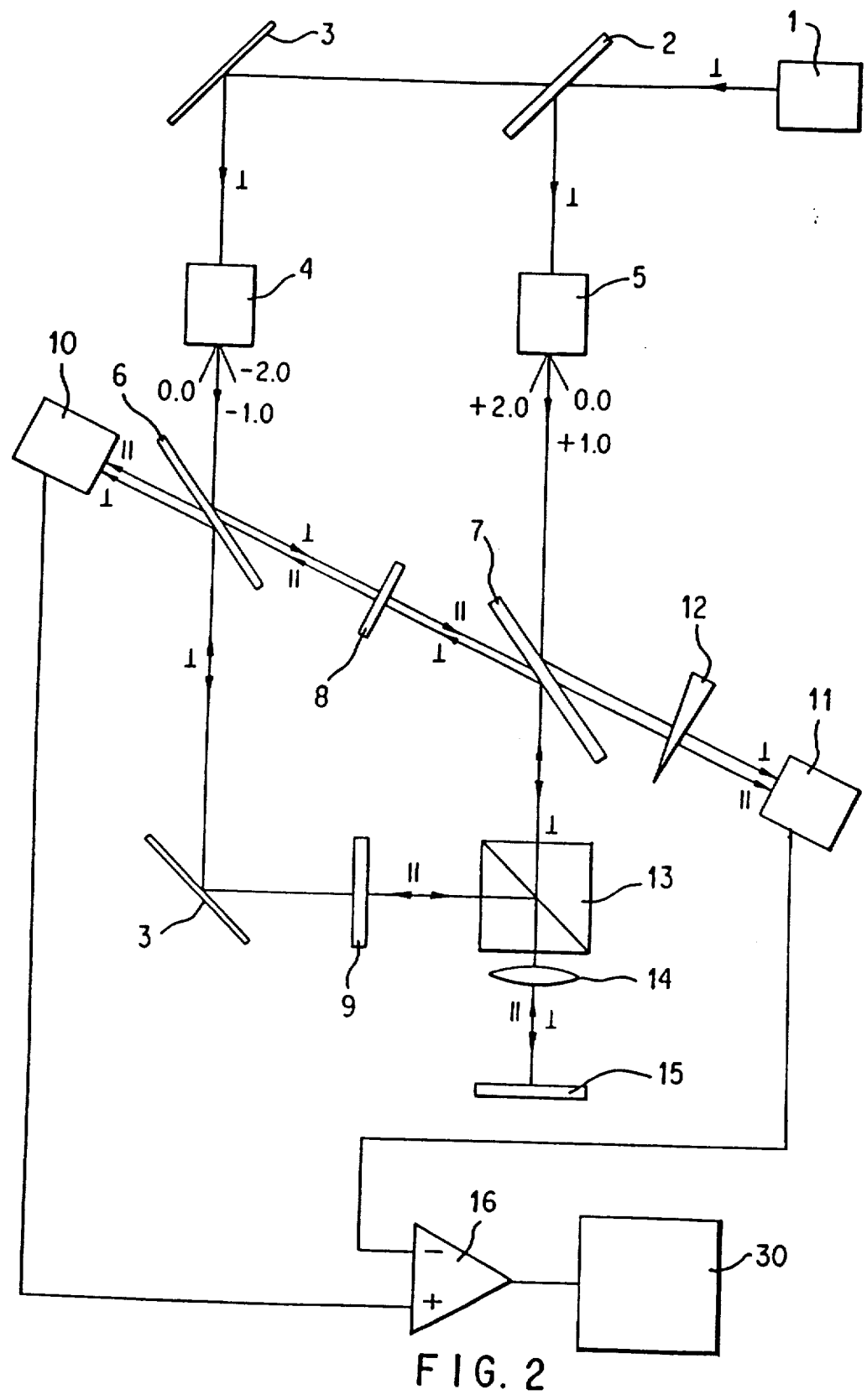
Figure 3:
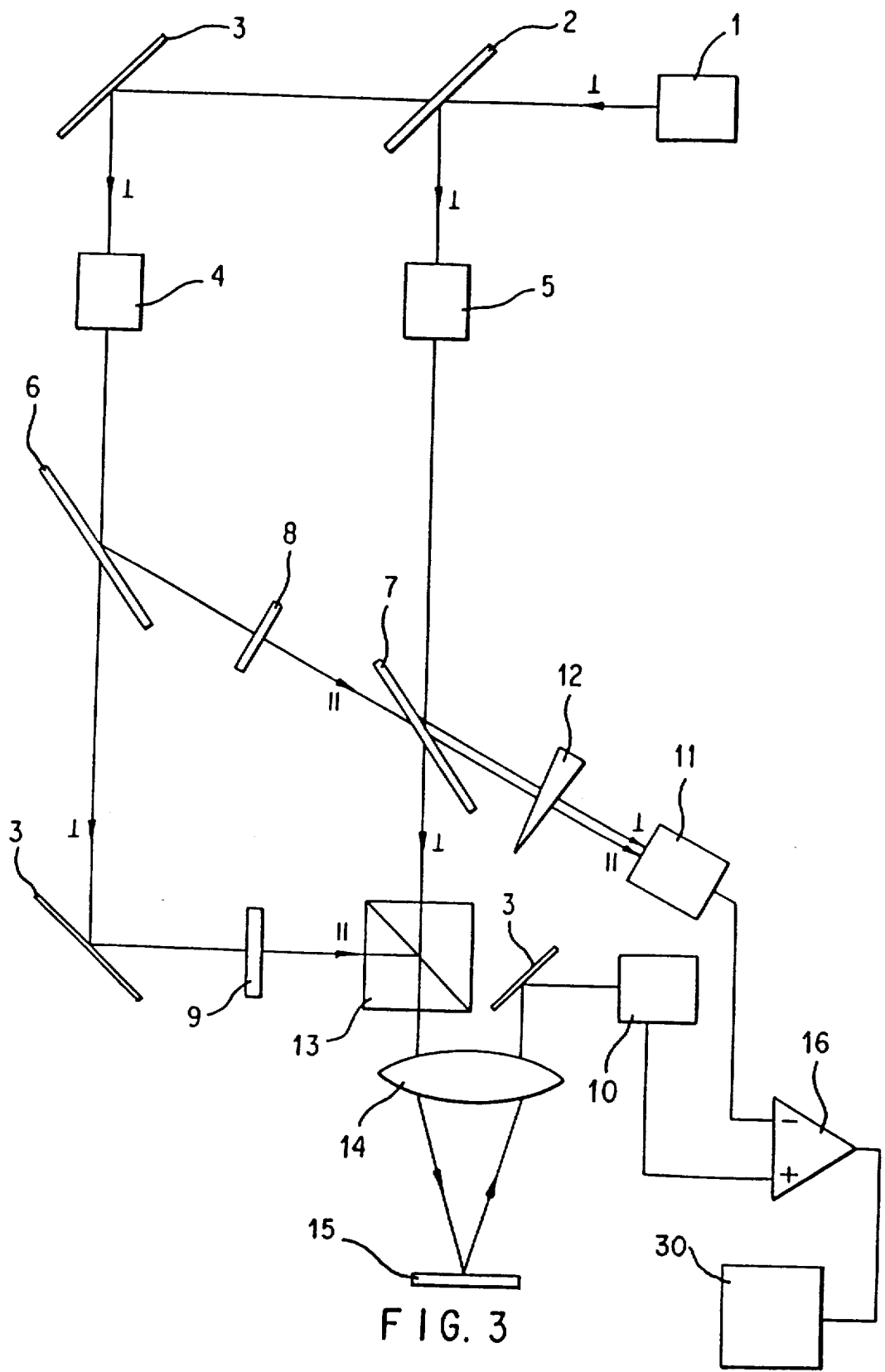
Figure 4:
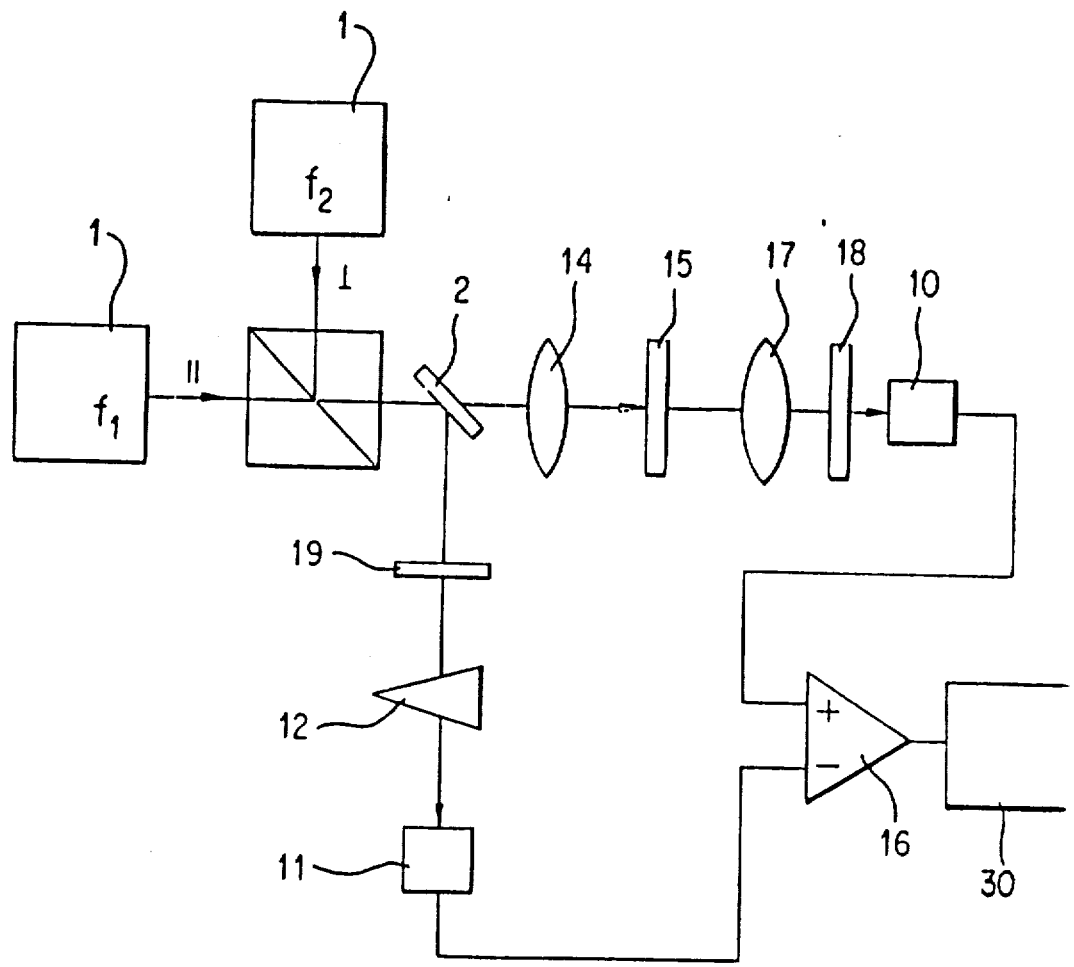

FIG. 4, which shows the transmission mode with two separate laser sources 1. Additional optical polarization elements are used in order to screen those parts of the laser beam for recording which permit the phase shift of the response signal with respect to the modulation signal of the excitation beam to be determined. After its modulation, which is realized in the embodiment of FIG. 4 by the modulation of two semiconductor lasers which are polarized perpendicularly to one another, the beam, assembled by means of the polarization separating beam-splitting prism 13 passes through the focussing objective 14 and reaches the object 15. From this incident beam, a part of exactly one of the two partial beams is passed by means of the semitransparent mirror 2 and a polarization filter 19 via the element 12 with the controllable transmission to the reference detector 11 for obtaining the reference signal. The portion of the laser beam, transmitted through the object 15 reaches the measurement detector 10 by way of the optical system 17 that is equivalent to the objective 14 and a further polarization filter 19, which is oriented in exactly the same way as the polarization filter 18. The further processing is identical with that described in the previous three examples and permits phase analysis in addition to amplitude analysis.

We claim:

1. In the method of thermowave analysis in which a laser beam is directed onto an object to be analyzed, whereby the intensity of said laser beam is modified by the reaction of the object to the energy of the beam directed thereto, and modification of the beam is detected with a measurement detector by way of a focusing objective, the improvement comprising modulating the intensity of the laser beam, before it strikes the object, to have a modulation spectrum that contains two discrete frequencies ($f_1$; $f_2$) and measuring the optical response of the object by measuring the amplitude of a mixed frequency which is produced by the reaction of said object to the two modulation frequencies ($f_1$; $f_2$) at the output of the measurement detector, with a frequency-selective device.

2. The method of claim 1 comprising generating the laser beam with a laser diode, wherein said step of modulating comprises energizing said laser diode at both of said modulation frequencies ($f_1$; $f_2$).

3. The method of claim 1 wherein said step of modulating comprises passing the laser beam in the beam path between the laser source and the objective through an optical modulator, and supplying signals at both modulation frequencies ($f_1$; $f_2$) to said optical modulator.

4. The method of claim 1 comprising forming the laser beam from two partial beams which cannot interfere with one another and said step of modulating comprises intensity modulating each of the beams with a separate one of the two frequencies ($f_1$; $f_2$).

5. The method of claim 4 wherein said step of forming the laser beam comprises producing the two partial beams with two mutually independent laser sources.

6. The method of claim 4 wherein said step of intensity modulating said beams comprises passing each of the two partial beams through acoustooptical modulating means.

7. The method of claim 4 comprising polarizing the two partial beams perpendicularly to one another so that they cannot interfere with one another.

8. The method of claim 4 comprising beam splitting the output of a single laser source to produce said partial beams, and processing said beams to eliminate interference between the partial beams before they are brought together.

9. The method of claim 8 wherein said step of eliminating interference comprises selecting the frequencies $f_1$ and $f_2$ to have a large wavelength difference therebetween.

10. The method of claim 8 wherein said step of eliminating interference comprises employing different diffraction orders with the two discrete frequencies ($f_1$; $f_2$) in said step of modulating the intensity of the laser beam.

11. The method of claim 8 wherein said step of eliminating interference comprises employing different carrier frequencies in said step of modulating the intensity of the laser beam.

12. The method of claim 8 wherein said step of eliminating interference comprises setting the polarization direction of the two partial beams to be perpendicular to one another.

13. The method of claim 1 wherein said step of measuring comprises measuring the amplitude of the difference frequency of the two modulation frequencies ($f_1$; $f_2$) in said output of said measurement detector.

14. The method of claim 1 comprising measuring the amplitude and phase shift with respect to said modulation frequencies ($f_1$; $f_2$) of the summation frequency of the two modulation frequencies ($f_1$; $f_2$) in the output of the measuring detector.

15. The method of claim 1 comprising decoupling a portion of the light directed onto the object and directing the decoupled light onto a reference detector for producing a reference signal and comparing said reference signal and the output of said measurement detector.

16. The method of claim 1 comprising forming the laser beam from two partial beams, which are incapable of interfering with one another and said step of modulating comprises intensity modulating said partial beams with separate ones of the two frequencies ($f_1$; $f_2$), and further comprising polarizing the partial beams perpendicularly to one another, before they are brought together and analyzed, and precisely measuring one of the two partial beams in one of the detectors.

17. The method of claim 16 wherein said step of measuring comprises analyzing the amplitude and phase of said one partial beam with a phase-sensitive rectifier.

18. In an apparatus for thermowave analysis comprising a source of a laser beam, means for focusing said beam by way of an objective onto an object to be investigated, optical imaging means in the beam path following the interaction of the beam with the object, and a measurement detector for detecting the intensity of energy received from said object via the optical imaging means resulting from the reaction of the object to the energy directed thereto, the improvement wherein the laser source comprises means for providing a laser beam with two discrete frequencies ($f_1;f_2$) in the modulation spectrum of the beam, and a frequency-selective device connected to exclusively select a mixed frequency of the two modulation frequencies ($f_1;f_2$) produced by said object reaction, said frequency-selective device being coupled to the output of the measurement detector to determine the amplitude of said mixed frequency.

19. The apparatus of claim 18 wherein the laser source is a laser diode and means for applying at both modulation frequencies ($f_1;f_2$) to said laser diode.

20. The apparatus of claim 18 for measurement in a transmission mode, comprising an optical system which is optically equivalent to said objective, the optical system and the measurement detector being connected in series in that order to receive energy from the object on the same optical axis.

21. The apparatus of claim 18 for measurement in a reflection mode wherein the laser beam is reflected from the object and is accompanied with reaction products, and said frequency-selective device is positioned in the path of the reflected beam and reaction products.

22. The apparatus of claim 18 further comprising a differential amplifier with an inverting input connected to a reference detector and a noninverting input connected to said measurement detector, the input of the reference detector being decoupled from the laser beam of the laser source by a semitransparent mirror, said frequency-selective device being coupled to the output of said differential amplifier.

23. The apparatus of claim 18 wherein the laser source is comprised of an unmodulated laser and a modulating optical element, and means for applying energy at the two modulation frequencies ($f_1;f_2$) to the modulating optical element 24. The apparatus of claim 23 wherein the modulating optical element is an acoustooptical modulator.

25. In an apparatus for thermowave analysis in which a laser beam is focused by way of an objective onto an object to be analyzed, whereby the beam interacts with the object, optical imaging means positioned to receive the results of the interaction of the laser beam with the object, and a measurement detector positioned to receive the output of said optical imaging means for detecting the intensity of the energy caused by reaction of the laser beam with the object, the improvement comprising a semitransparent mirror positioned in the path of the laser beam before it impinges on said object, said semitransparent mirror producing two equivalent partial beams, means for eliminating the ability of the two partial beams to interfere with one another, a separate optical element for modulating the intensity of each partial beam, the two modulating optical elements having different modulating frequencies ($f_1,f_2$), means for decoupling the laser beam reflected by the object in both partial beams, a beam-splitting prism for combining the two partial beams and disposed before the objective and a frequency-selective element for determining the amplitude of a mixed frequency produced by reaction of the object with the laser beam modulated with the modulation frequencies ($f_1;f_2$), said frequency-selective element being connected in series with the measurement detector.

26. The apparatus of claim 25, wherein
the means for eliminating the ability of the two partial beams are polarized in the same direction after splitting thereof by said semitransparent mirror; and further comprising
a separate glass plate mounted in the path of each of the partial beams at an angle lower than the Brewster angle, so that the portions of the beams reflected by the glass plates are reflected along a common axis, and a $\lambda$ plate in one of the partial beam paths between the respective glass plate and the beam-splitting prism.

27. The apparatus of claim 26 comprising
a reference detector is provided on said common axis,
the measurement detector being positioned on said common axis of glass plates and opposite the reference detector with respect to the space between the glass plates and
the beam-splitting prism comprises a polarization separator for a beam portion reflected by the object.

28. The apparatus of claim 27 further comprising an element with a controllable transmission mounted immediately in front of the reference detector in order to equalize the temporal average value of the difference between the measurement detector signal and the reference detector signal to zero.

29. The apparatus of claim 26 wherein, for the complete decoupling of the beam incident on and reflected at the object
the laser beam incident on the object is oriented to provide a beam parallel to the axis of the objective, so that the beam which is reflected at the object proceeds centrosymmetrically with respect to the axis of the objective, and
the measurement detector is disposed in the path of the reflected beam which emerges parallel to said axis.

30. In an apparatus for thermowave analysis, in which a laser beam is focused by way of an objective onto the object to be analyzed, and optical imaging means are disposed in the path of the beam after its interaction with the object, and a measurement detector is provided for detecting the intensity of the output of the optical imaging means, whereby the beam is modulated by the reaction of the object to the energy directed thereto, the improvement comprising
means for producing the laser beam from the beams of two separate laser sources, which are intensity modulated differently, each with a different frequency ($f_1; f_2$),
a beam-splitting prism mounted before the objective to combine the beams of the two laser sources and
a frequency-selective device for determining the amplitude of a mixed frequency of the frequencies ($f_1;f_2$) produced by the object due to a reaction with the laser beam, said frequency-selective device being connected in series with the measurement detector.

31. The apparatus of claim 30 comprising a semitransparent mirror positioned to have a reflected beam portion strike a reference detector, the mirror being disposed between the beam-splitting prism and the objective, whereby a portion of the beam reflected by the semitransparent mirror strikes the reference detector, the reference detector and the measurement detector being connected to separate inputs of a differential amplifier, the differential amplifier being connected ahead of the frequency-selective device.

32. The apparatus of claim 31 wherein
the two laser sources comprise means for producing two beams that are polarized perpendicularly with respect to one another, and
wherein the beam-splitting prism comprises a polarization separator, and further comprising
separate polarization filters having the same polarization and positioned ahead of the measurement detector and the reference detector, respectively.

* * * * *

UNITED STATES PATENT AND TRADEMARK OFFICE
CERTIFICATE OF CORRECTION

PATENT NO. : 5,206,710

DATED : April 27, 1993

INVENTOR(S) : Hans-Dieter Geiler et al

It is certified that error appears in the above-indentified patent and that said Letters Patent is hereby corrected as shown below:

The title page should be deleted to appear as per attached title page.

The sheets of drawings should be deleted to appear as per attached pages.

Signed and Sealed this

Fifth Day of April, 1994

Attest:

BRUCE LEHMAN

*Attesting Officer*     *Commissioner of Patents and Trademarks*

United States Patent [19]

Geiler et al.

[11] Patent Number: 5,206,710
[45] Date of Patent: Apr. 27, 1993

[54] METHOD AND APPARATUS FOR THERMOWAVE ANALYSIS

[75] Inventors: Hans-Dieter Geiler; Matthias Wagner; Peter Kowalski, all of Jena, German Democratic Rep.

[73] Assignee: Jenoptik Jena GmbH, Jena, Fed. Rep. of Germany

[21] Appl. No.: 765,646

[22] Filed: Sep. 25, 1991

[30] Foreign Application Priority Data

Nov. 2, 1990 [DE] Fed. Rep. of Germany ....... 4035266

[51] Int. Cl.⁵ .......................................... G01N 21/17
[52] U.S. Cl. .................................. 356/432; 356/447
[58] Field of Search ................ 356/432, 432 T, 445, 356/447; 250/351, 339, 338.5; 374/5, 57

[56] References Cited

U.S. PATENT DOCUMENTS

| | | | |
|---|---|---|---|
| 4,044,257 | 8/1977 | Kreuzer | 356/432 |
| 4,579,463 | 4/1986 | Rosencwaig et al. | 356/432 |
| 4,634,290 | 1/1987 | Rosencwaig et al. | 356/432 |
| 4,636,088 | 1/1987 | Rosencwaig et al. | 356/432 |

Primary Examiner—Richard A. Rosenberger
Attorney, Agent, or Firm—Jordan and Hamburg

[57] ABSTRACT

A method and apparatus for thermowave analysis employs a single laser beam, which has an additive, two-frequency, intensity modulation, and is directed onto the object. The amplitude of the mixed frequency of the discrete modulation frequencies, which is not contained in the exciting beam, is analyzed as response signal. By obtaining a reference signal from the exciting beam and forming the difference between this exciting beam and the measurement signal, noise suppression and a lowering of the limit of sensitivity are achieved in an advantageous manner.

32 Claims, 4 Drawing Sheets

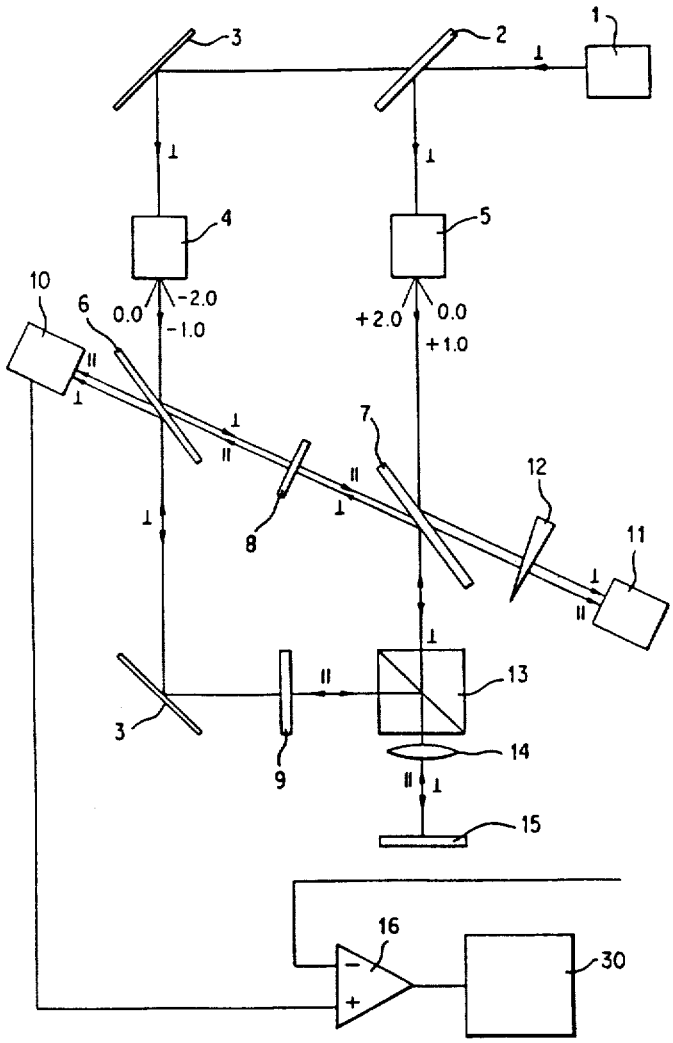

UNITED STATES PATENT AND TRADEMARK OFFICE
CERTIFICATE OF CORRECTION

PATENT NO. : 5,206,710
DATED : April 27, 1993
INVENTOR(S) : Geiler, et al

It is certified that error appears in the above-indentified patent and that said Letters Patent is hereby corrected as shown below:

The title page should be deleted to appear as per attached title page.

This certificate supersedes The Certificate of Correction issued April 5, 1994.

Signed and Sealed this

Twenty-eighth Day of June, 1994

Attest:

BRUCE LEHMAN

Attesting Officer

Commissioner of Patents and Trademarks

United States Patent [19]

Geiler et al.

[11] Patent Number: 5,206,710
[45] Date of Patent: Apr. 27, 1993

[54] METHOD AND APPARATUS FOR THERMOWAVE ANALYSIS

[75] Inventors: Hans-Dieter Geiler; Matthias Wagner; Peter Kowalski, all of Jena, German Democratic Rep.

[73] Assignee: Jenoptik Jena GmbH, Jena, Fed. Rep. of Germany

[21] Appl. No.: 765,646

[22] Filed: Sep. 25, 1991

[30] Foreign Application Priority Data

Nov. 2, 1990 [DE] Fed. Rep. of Germany ....... 4035266

[51] Int. Cl.⁵ .......................................... G01N 21/17
[52] U.S. Cl. ..................................... 356/432; 356/447
[58] Field of Search .................. 356/432, 432 T, 445, 356/447; 250/351, 339, 338.5; 374/5, 57

[56] References Cited

U.S. PATENT DOCUMENTS

| 4,044,257 | 8/1977 | Kreuzer | 356/432 |
| 4,579,463 | 4/1986 | Rosencwaig et al. | 356/432 |
| 4,634,290 | 1/1987 | Rosencwaig et al. | 356/432 |
| 4,636,088 | 1/1987 | Rosencwaig et al. | 356/432 |

Primary Examiner—Richard A. Rosenberger
Attorney, Agent, or Firm—Jordan and Hamburg

[57] ABSTRACT

A method and apparatus for thermowave analysis employs a single laser beam, which has an additive, two-frequency, intensity modulation, and is directed onto the object. The amplitude of the mixed frequency of the discrete modulation frequencies, which is not contained in the exciting beam, is analyzed as response signal. By obtaining a reference signal from the exciting beam and forming the difference between this exciting beam and the measurement signal, noise suppression and a lowering of the limit of sensitivity are achieved in an advantageous manner.

32 Claims, 4 Drawing Sheets

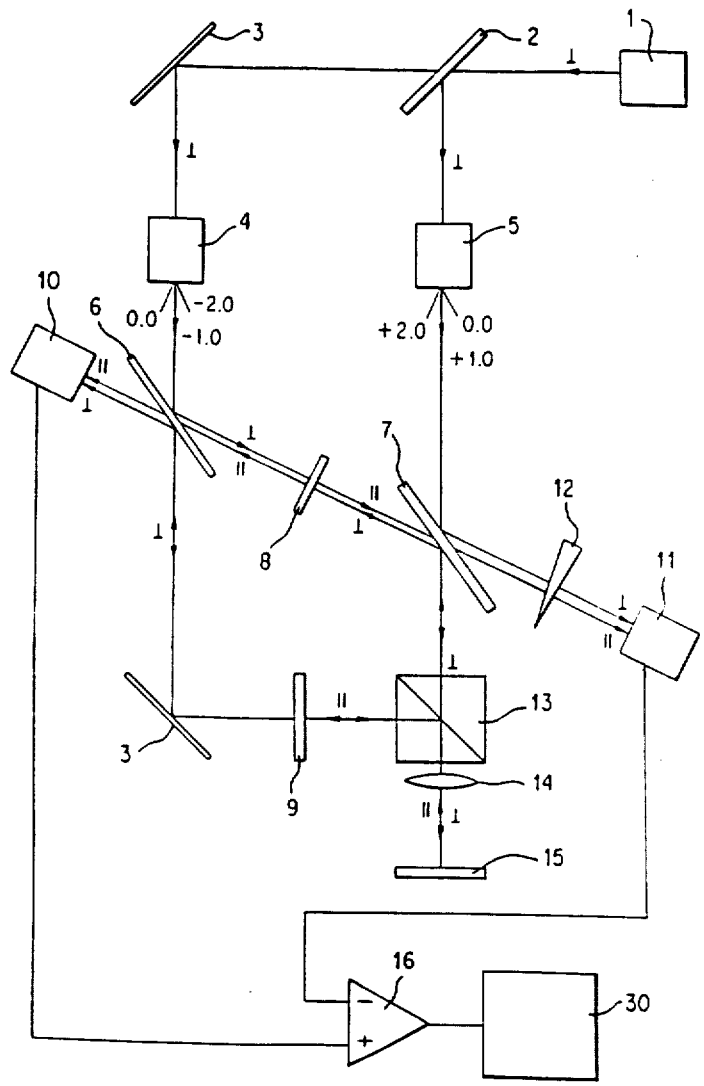

UNITED STATES PATENT AND TRADEMARK OFFICE
CERTIFICATE OF CORRECTION

PATENT NO. : 5,206,710

DATED : April 27, 1993

INVENTOR(S) : Geiler, et al

Psge 3 of 7

It is certified that error appears in the above-indentified patent and that said Letters Patent is hereby corrected as shown below:

The sheets of drawings, consisting of Figures 1-4 should be deleted to appear as per attached sheets.